US006905459B2

(12) United States Patent
Humphries, Jr.

(10) Patent No.: US 6,905,459 B2
(45) Date of Patent: Jun. 14, 2005

(54) DEVICE FOR TREATING ERECTILE DYSFUNCTION

(75) Inventor: Arthur L. Humphries, Jr., 3128 Walton Way, Augusta, GA (US) 30309-3265

(73) Assignee: Arthur L. Humphries, Jr., Augusta, GA (US)

(*) Notice: Subject to any disclaimer, the term of this patent is extended or adjusted under 35 U.S.C. 154(b) by 0 days.

(21) Appl. No.: 10/410,502

(22) Filed: Apr. 9, 2003

(65) Prior Publication Data

US 2004/0204626 A1 Oct. 14, 2004

(51) Int. Cl.⁷ ............................................ A61F 5/00
(52) U.S. Cl. ................................. 600/38; 128/202.12
(58) Field of Search ..................... 600/38, 41, 21–22; 128/202.12, 205.26

(56) References Cited

U.S. PATENT DOCUMENTS

| | | | |
|---|---|---|---|
| 1,225,341 A | | 5/1917 | Lederer |
| 3,744,486 A | | 7/1973 | Wilson |
| 3,903,869 A | * | 9/1975 | Bancalari ............... 128/202.12 |
| 4,378,008 A | | 3/1983 | Osbon, Sr. |
| 4,612,916 A | * | 9/1986 | Akers et al. .................. 600/21 |
| 4,856,498 A | | 8/1989 | Osbon |
| 5,115,800 A | | 5/1992 | Matejevic et al. |
| 5,133,339 A | | 7/1992 | Whalen et al. |
| 5,421,808 A | | 6/1995 | Osbon et al. |
| 5,865,722 A | * | 2/1999 | Heng ........................... 600/21 |
| 6,036,635 A | | 3/2000 | Altshuler |
| 6,099,463 A | | 8/2000 | Hockhalter |

RE36,958 E    11/2000  Gamow

OTHER PUBLICATIONS

Brown E. Goei J S, Greenfield ADM, Plassaras GC. Circulatory Responses To Simulated Gravitational Shifts of Blood in Man Induced by Exposure of The Body Below The Iliac Crests To Sub-Atmospheric Pressure, *J. Physiol.* 1966; 183:607–627. ref. 106.

Cooper KH, Ord J.W. Physical Effects of Seated and Supine Exercise With and Without Subatmospheric Pressure Applied to the Lower Body, *Aerospace Medicine*, 1968; 30: 481–484. ref 109.

Stevens PM, Lamb LE. Effects of Lower Body Negative Pressure on the Cardiovascular System, *American Journal of Cardiology* 1965; 16: 506–515. Ref. 87.

Nadig PW et al. Noninvasive Device to Produce and Maintain an Erection–State., *Urology* 1986; 27: 126–131. ref 20.

Lewis R W, Witherington R. External vacuum therapy for erectile dysfunction: use and results., *World J Urology* 1997; 15: 78–82. ref 33.

Witherington R. Vacuum Constriction Device for Management of Erectile Impotence., *Urology* 1989; 141: 320–322. ref 19a.

* cited by examiner

Primary Examiner—John P. Lacyk
(74) Attorney, Agent, or Firm—Dority & Manning, P.A.

(57) ABSTRACT

A device for aiding in stimulating blood flow in a sexual organ of a user leading to erection. The device includes a chamber adapted to receive and enclose a user's body from adjacent the waist of the user to adjacent the upper thighs. A source of vacuum is applied to the chamber for creating a negative pressure within the chamber while permitting the user's arms to be extended into the chamber for manipulating the sexual organ.

8 Claims, 3 Drawing Sheets

DEVICE FOR TREATING ERECTILE DYSFUNCTION

BACKGROUND OF THE INVENTION

A substantial amount of research has been conducted and reported emphasizing the physiological and psychological benefits of sexual activity including sexual activity between partners as well as masturbation. Most physicians believe that masturbation is healthful as long as religious, moral, and psychological concerns—fear of sin or feelings of guilt—can be put aside. Some of the reports indicate that ejaculation and orgasm three times a week is healthful. Even once or twice a week, sex increases levels of immunoglobulin and thereby helps prevent tension and possible other illnesses. Some of the reports have indicated that sex once a day might add several years to a man or woman's life. Most of these authorities do not specifically state that solo masturbation is as helpful as is sexual intercourse with a partner, but masturbation is increasingly viewed not only as a response to the loss of sexual contact with a partner, but also as a natural and ongoing supplemental activity within a relationship. It is generally thought that masturbation as well as sexual intercourse reduce tension and stress in both men and women.

There have been many devices developed for providing blood engorgement of both the penis for men and the clitoris of women to aid them in sexual activity with a partner. Some of these attempts are disclosed in the following patents: U.S. Pat. Nos. 6,099,463; 4,856,498; 4,378,008; 3,744,486; 1,225,341; 6,036,635; 5,115,800; and RE 36,958. In addition to the patents, there are numerous articles discussing the problems with erectile dysfunction and the fact that sexual activity has both physiological and psychological benefits. As reported there are many persons, especially older men and women, who suffer from erectile dysfunction.

Accordingly, it is an object of the present invention to provide an apparatus which aids a user in obtaining an erection to facilitate masturbation in an attempt to have an orgasm.

SUMMARY OF THE INVENTION

A device for aiding and stimulating blood flow in the sexual organ of a user leading to an erection for facilitating masturbation. The device may be used by both men and women, and when reference is made to a sexual organ in the claims and in the specification hereof, it could include both the penis of the male and the clitoris of a female.

The device includes a chamber adapted to receive and enclose a user's body from adjacent the waist of the user to adjacent the upper thighs. The chamber includes a front wall and a rear wall joined by side walls, a top, and a bottom wall. The rear wall has two openings through which the legs of the user extend. The front wall has a main opening for allowing the user to insert his lower body into the chamber allowing the user's legs to extend through openings in the rear walls. A source of vacuum is coupled to the chamber for creating a negative pressure within the chamber. Arm openings are provided in the front wall through which the user's arms extend in order for the user to touch and/or massage his/her sexual organ. Air seals are provided between the openings in the rear wall and the user's legs and similar air seals are provided between the main opening and the user's body and the arm openings and the arms of a user.

Once the user extends his torso into the chamber with his legs extending out the rear, he inserts his arms through the openings provided in the front wall to touch and manipulate his sexual organ to initiate sexual arousal. After sexual arousal begins, a switch is operated to turn on a vacuum pump to place a negative pressure within the chamber. When a negative pressure is applied to the chamber, it assists in causing the engorgement of blood into the penis or clitoris of the user to produce an erection. Once an erection has occurred, the user through manual manipulation either by the hands or any other suitable mechanical tool manipulates the sexual organ until ejaculation and/or orgasm occurs.

DETAILED DESCRIPTION OF THE PREFERRED EMBODIMENT

Figure 1:
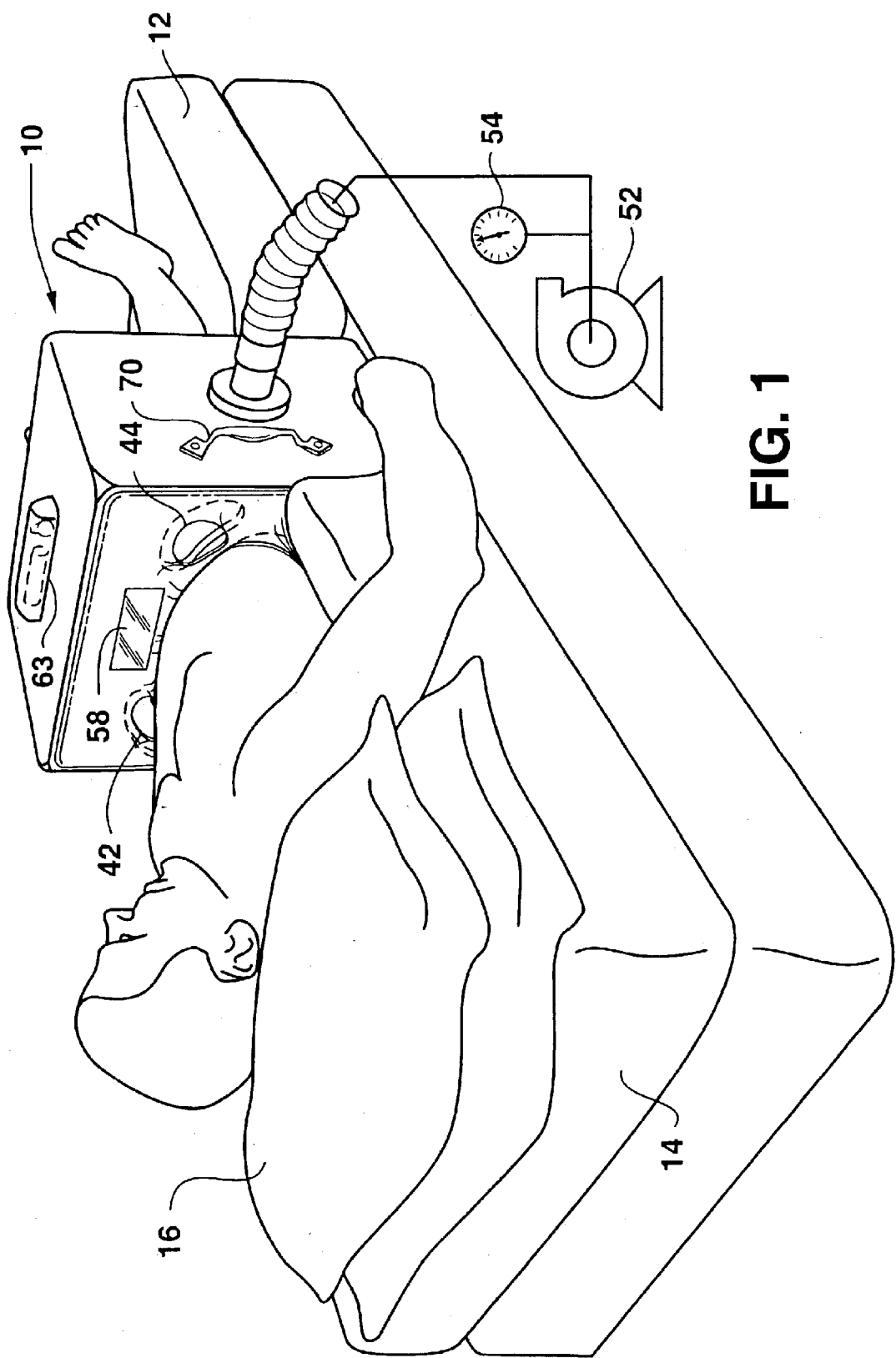
FIG. 1 is perspective view of a preferred embodiment illustrating a user utilizing the invention.

Referring in more detail to FIG. 1 of the drawings, there is a device for aiding in stimulating blood flow into the penis of a male or the clitoris of a female. Such is accomplished by producing a negative pressure over the user's body in the housing extending from about the waist to the thighs. After the user has performed preliminary manipulation of his sexual organ, the chamber is placed under a vacuum which causes the walls of the corpora cavemosa to distend and overfill with blood. The engorgement leads to a very hard erection of the penis or clitoris usually within one or two minutes. The apparatus includes a chamber generally designated by the reference character 10 into which a user extends his body. The chamber 10 for purposes of comfort, is inserted between two mattresses 12 and 14 so that the user's body can extend conveniently through the openings provided in the chamber. Suitable pillows 16 are provided for additional comfort to the user to aid him in lying in a supine position.

The chamber includes a front wall 18 and a rear wall 20 joined by side walls 22 and 24, a top 26, and a bottom 28. The rear wall has a pair of openings 32 provided therein through which the user's legs extend. Only one of the openings is shown.

A main opening 34 is provided in the front wall 18 for enabling the user to insert his torso through the housing. The opening 34 is of sufficient size to permit the hips to pass therethrough into the interior of the chamber and to extend around the waist portion of the user. Two additional openings 36 and 38 are provided in the front wall 18 for permitting the user to insert his arms therethrough into the cavity of the chamber. In order to provide a substantially sealed chamber, a latex sheet 39 is attached by any suitable means to the front wall and has a centrally located opening 40 that extends over the opening 34 in the front wall. It also has a pair of openings 42 and 44 provided therein that extend over the openings 36 and 38 respectively for permitting the arms of the user to pass therethrough. As a result of the latex material being elastic and flexible when the arms of the user and the torso are inserted through the holes therein, a seal is produced around the arms and torso. The opening 40 in the latex sheet 39 has a flap portion 46 that is joined adjacent the lower side of the opening so that it can be pulled down by any suitable means such as a strap 48 when the user is inserting his body therethrough.

The latex sheet 39 provides a seal over the front wall of the chamber. An additional latex member 50 is attached to the rear wall of the chamber and has circular openings 51 provided therein which are slightly smaller than the openings 32 provided in the rear wall so as to produce a seal around the thighs once they are inserted therethrough. The elastic flexible sheet 50 may be attached to the rear wall in any suitable manner such as through taping or by adhesive.

While it is shown that a latex sheet is being used to provide seals around the openings for receiving the arms, torso, and legs, it is to be understood that other suitable sealing members could be used such as an inflated flexible rubber tubular member or elastic material as long as it provides a seal around the legs, torso, and arms when a negative pressure is applied to the interior of the chamber.

A negative pressure is produced in the chamber by a vacuum pump 52 for evacuating air from the chamber that has a pressure gauge 54 connected to the conduit 56 that is attached to the side wall of the chamber. Any suitable electrical switch can be used with the vacuum pump for turning the vacuum pump on. A foot operated switch is preferred since it does not require the user to remove his arms from the chamber.

Figure 2:
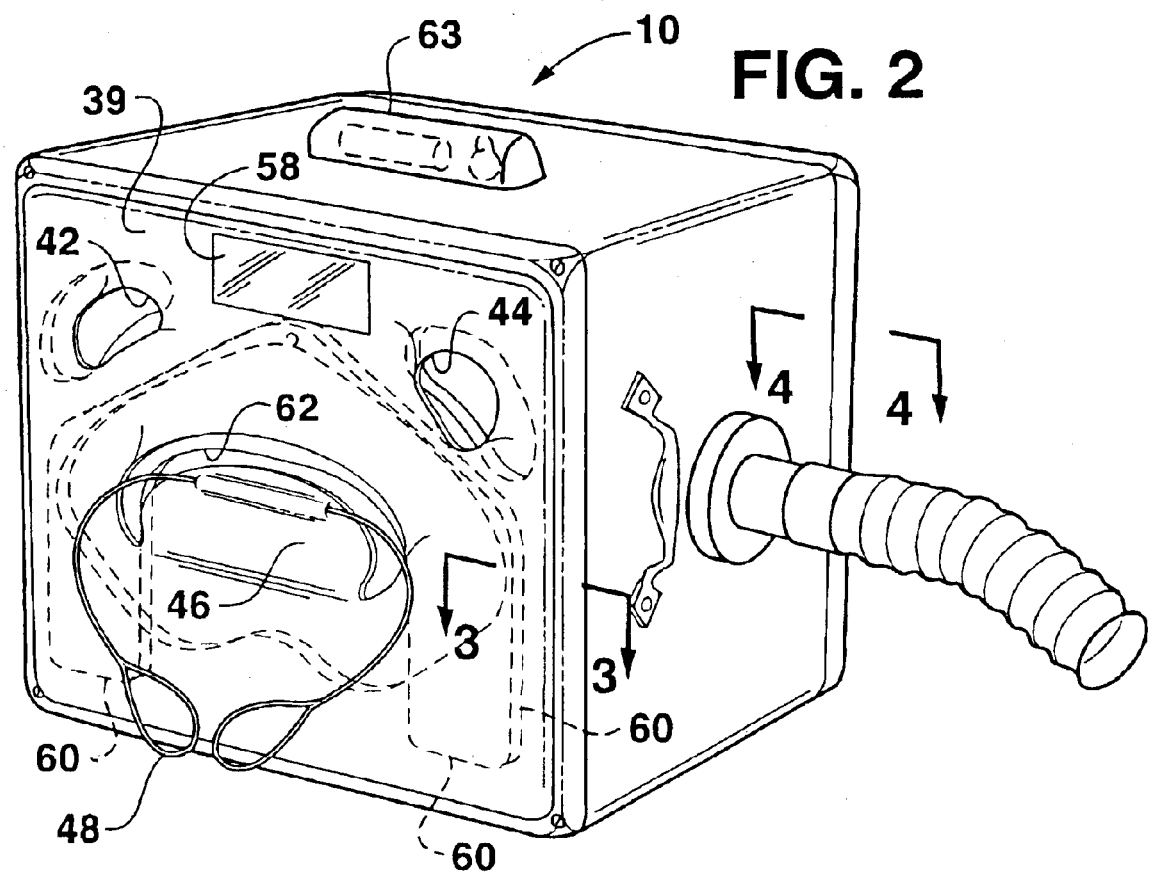
FIG. 2 is an enlarged perspective view of a chamber that can be used for stimulating the user's sexual organ.
Figures 3, 4:
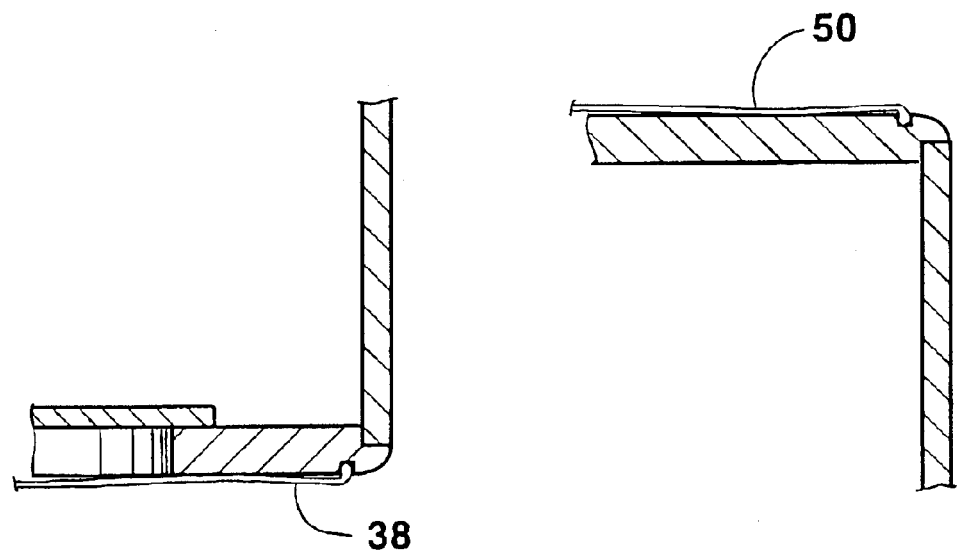
FIG. 3 is a sectional view taken along line 3—3 of FIG. 2.
FIG. 4 is a sectional view taken along line 4—4 of FIG. 2.
Figure 5:
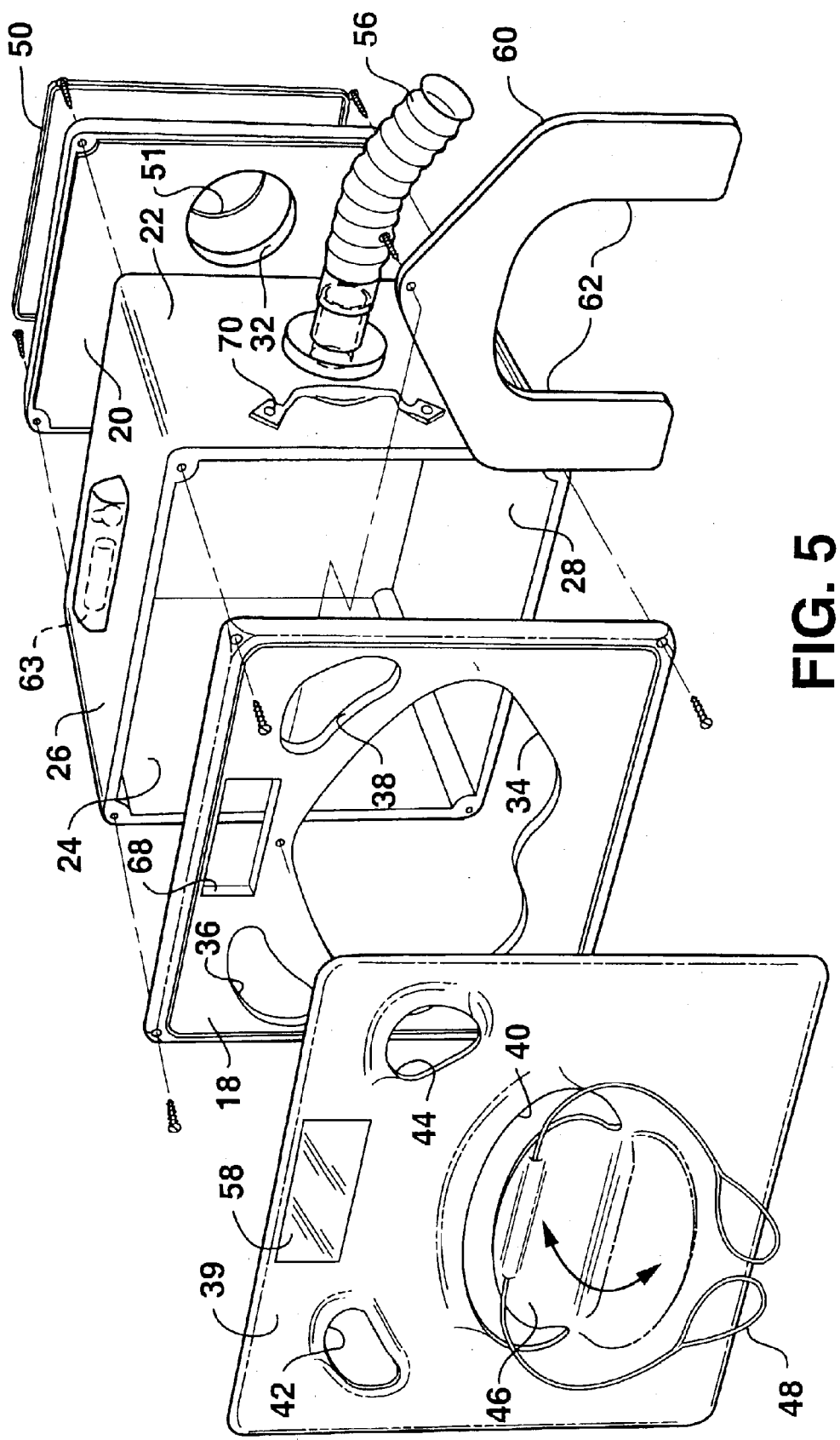
FIG. 5 is an exploded view of the apparatus shown in FIG. 1.

A transparent viewing window 68 is provided in the front wall 18 of the chamber for permitting the user to see inside the chamber. The viewing window 58 is shown in the latex sheet 39. The transparent viewing window 58 however, could be inserted in the front wall opening 68. If this is the case, then it would be necessary for the latex sheet to be secured to the front wall slightly below the viewing window 68. The viewing window 58 may be constructed of any suitable transparent material that can be attached to the latex sheet 39 by any suitable adhesive means. A battery operated light 63 is provided on top of the chamber for illuminating the inside of the chamber. Since users of the apparatus will be of different sizes, in order to aid in producing positive seals around the users torso, a baffle plate 60 can be inserted between the front wall 18 and the flexible sheet 39. The baffle plate 60 has a contoured cut out 62 which produces a closer fit with the abdomen and the ribs of the user. Such minimizes the chance that the flexible elastic sheet 39 will be involuted into the chamber by the negative pressure. Other types of baffle plates could be utilized, and while the baffle plate as shown in FIG. 5 is attached to the front wall by a screw or peg, it is to be understood that baffle plates could be supported between vertically extending tracks so that it could be lowered and raised by the user after inserting his body into and before taking his body out of the chamber. As can be seen in FIG. 2, the openings in the front wall shown in phantom lines are larger in diameter and length than the openings provided in the elastic flexible sheet 39 so that the sheet 39 is pulled securely around the arms and the torso of the user to provide an air seal. It has been found that the preferred negative pressure in the chamber should be approximately -160 mmHg. While a -160 mmHg is the preferred pressure, it has been found that a pressure between a -120 mmHg to a -210 mmHg is suitable.

While the chamber has been shown to be constructed in a single unitary housing having a top, side walls, and a bottom, it is to be understood that the chamber could be constructed into separable portions such as a bottom half and a top half that are secured together by any suitable means such as a hinge connection that permits the chamber to be closed around the user's body when he is positioned therein. This would require different types of seals from the flexible elastic sheets shown but it is to be understood that any suitable seals could be used for providing a seal around the limbs and the torso of the body.

Handles 70 are provided on the side walls for permitting the user to grip when pulling his body into the chamber.

In operation, when a user desires to use the device for aiding in obtaining an erection in his penis, he slides his legs through the opening 40 provided in the sheet 39 while pulling the flap 46 downwardly with the straps 48 over his buttocks. Once the user pulls himself into the chamber so that his legs extend out the rear of the chamber and the front wall 18 is located approximately at his waist, he is in a position to begin the mental foreplay that is preferred prior to applying suction to the chamber. This mental foreplay can include stimulating photographs and/or manually manipulating the sexual organ with his hands. Once the user becomes manually stimulated, he depresses a switch with his foot or any other means to turn on the vacuum pump. The vacuum pump creates a negative pressure within the chamber that increases blood flow into the penis that produces an erection. At this point in time, the user can masturbate to obtain an orgasm or if he prefers, he can place a restrictive device such as a rubber band on the penis adjacent the junction of the body so as to hold the penis in an erected position to enable him to complete the sexual activity with a partner.

While the above description has been primarily related to a male and the penis sexual organ, it is to be understood that the same procedure could be used by a female permitting her to have an erection of the clitoris by means of blood trapped therein when exposed to the negative pressure in the chamber.

While the chamber 10 as shown in the drawings is a substantially rectangular shaped chamber, it is understood that the chamber that includes the top and side walls could be made in tubular shape. An elongated tubular pipe of substantially the same diameter as the height of the chamber could be utilized with front and rear walls through which the user inserts his torso, arms, and legs. If such were the case, it would still be desirable to have a viewing window in the front wall to allow the user to see inside the chamber.

The dimension of the chamber could be varied to accommodate persons of different sizes.

If it is preferred that the viewing window 58 should be in the front wall 68 rather than in the latex sheet 39, then the height of the front wall should be increased to provide adequate space between the viewing window 68 and the openings 36 and 38 for the arms to permit the latex sheet 39 to be attached to the front wall. In one particular application, the latex sheet 39 is attached to the front wall by "duct tape".

While the preferred embodiment invention has been described using specific terms, such description is for illustrative purposes only, and it is to be understood that changes and variations may be made without departing from the spirit or scope of the following claims.

What is claimed is:

1. A device for aiding in stimulating blood flow into a sexual organ of a user leading to erection to facilitate masturbation comprising:

a chamber adapted to receive and enclose a user's body from adjacent the waist of the user to adjacent the upper thighs;

said chamber including a front wall and a rear wall;

said rear wall having openings through which the legs of the user extend;

a main opening provided in said front wall for allowing a user to insert his lower body into said chamber, allowing the user's legs to extend through said openings in said rear walls;

a source of vacuum coupled to said chamber for creating a negative pressure within said chamber;

arm openings provided in said front wall through which the user's arms extend in order for the user to touch his sexual organ (penis for a man and clitoris for a woman);

said rear wall being spaced from said front wall a sufficient distance so that said sexual organ of a user is located in said chamber between said front wall and said rear wall air seals provided between said openings in said rear wall and the user's legs; and air seals provided between said main opening and said user's body, and between said arm openings and the arms of said user whereby upon applying a negative pressure to said chamber, the sexual organ of the said user becomes engorged with blood to produce an erection.

2. The device as set forth in claim 1 wherein said air seal provided between said openings in said rear wall and said user's legs includes a flexible elastic sheet of material carried on said rear wall having openings therein through which said legs of the user extend to provide an air seal around the legs of said user.

3. The device as set forth in claim 1 wherein said air seals provided between said main opening and said user's body and between the arms of the said user and said arm openings includes a flexible elastic sheet extending over said front wall having openings therein through which the torso and arms of the user extend to provide an air seal around the arms and torso of said user.

4. The device as set forth in claim 1 further comprising a viewing port provided in said front wall through which the user can view his sexual organ.

5. The device as set forth in claim 3 further comprising:

a baffle plate provided between said front wall and said flexible elastic sheet;

said baffle plate having a cut out portion provided therein having an inner border corresponding generally to the shape of the user's abdomen to effectively reduce the size of said main opening in said front wall so as to aid said flexible sheet in providing a seal with the torso of the user.

6. The device as set forth in claim 3 further comprising a flexible flap carried by said flexible elastic sheet for aiding in providing a seal with the user's lower back.

7. The device as set forth in claim 1 further comprising a pressure gauge connected to said source of vacuum for indicating the air pressure within said chamber.

8. The device as set forth in claim 1 wherein said chamber is a unitary housing.

* * * * *